US012383898B2

United States Patent
Lueddecke et al.

(10) Patent No.: US 12,383,898 B2
(45) Date of Patent: Aug. 12, 2025

(54) NEGATIVE PRESSURE SWITCHING OF LIQUID

(71) Applicant: Hahn-Schickard-Gesellschaft fuer angewandte Forschung e.V., Villingen-Schwenningen (DE)

(72) Inventors: Jan Lueddecke, Neuenburg am Rhein (DE); Nils Paust, Freiburg im Breisgau (DE); Gustav Grether, Muehlheim (DE); Ehsan Mahmodi Arjmand, Freiburg (DE)

(73) Assignee: Hahn-Schickard-Gesellschaft fuer angewandte Forschung e.V., Villingen-Schwenningen (DE)

( * ) Notice: Subject to any disclaimer, the term of this patent is extended or adjusted under 35 U.S.C. 154(b) by 3 days.

(21) Appl. No.: 18/440,771

(22) Filed: Feb. 13, 2024

(65) Prior Publication Data

US 2024/0181450 A1    Jun. 6, 2024

Related U.S. Application Data

(63) Continuation of application No. PCT/EP2022/071973, filed on Aug. 4, 2022.

(30) Foreign Application Priority Data

Aug. 13, 2021   (DE) .................. 10 2021 208 891.0

(51) Int. Cl.
*B01L 3/00*   (2006.01)

(52) U.S. Cl.
CPC ... *B01L 3/50273* (2013.01); *B01L 2200/0621* (2013.01); *B01L 2200/0647* (2013.01);
(Continued)

(58) Field of Classification Search
CPC ......... B01L 3/502738; B01L 3/502753; B01L 2200/0621; B01L 2300/0681; B01L 2400/0409; B01L 2400/049
See application file for complete search history.

(56) References Cited

U.S. PATENT DOCUMENTS 6,063,589 A    5/2000  Kellogg et al.
7,819,138 B2 * 10/2010  Lee ..................... G05D 7/0694
                                                  422/501
(Continued)

FOREIGN PATENT DOCUMENTS

DE    102013215002 B3    6/2014
DE    102016207845 A1    11/2017
(Continued)

OTHER PUBLICATIONS

Gorkin, Robert, et al., "Suction-enhanced siphon valves for centrifugal microfluidic platforms", Microfluid Nanofluid 12, 345-354, DOI 10.1007/s10404-011-0878-2, 10 pp.
(Continued)

*Primary Examiner* — Eric Keasel
(74) *Attorney, Agent, or Firm* — Perkins Coie LLP; Michael A. Glenn

(57) ABSTRACT

A fluidics module has first fluidics structures having a first fluid chamber, second fluidics structures having a second fluid chamber, a first connection having a fluidic resistance between the first fluid chamber and the second fluid chamber, third fluidics structures having a third fluid chamber, a second connection having a barrier between the first fluid chamber and the third fluid chamber, a pressure compensation channel between the second fluid chamber and the third fluid chamber, and fourth fluidics structures having a fourth fluid chamber connected to the second fluidics structures via a third connection. Liquid can be transferred centrifugally from the first fluid chamber into the second fluid chamber.

(Continued)

Liquid from the second fluid chamber can be transferred under rotation into the fourth fluid chamber via the third connection to generate negative pressure in the third fluid chamber. The barrier can be overcome by liquid from the first fluid chamber due to the negative pressure generated to transfer liquid from the first fluid chamber into the third fluid chamber via the second connection.

7 Claims, 11 Drawing Sheets

(52) U.S. Cl.
CPC ... *B01L 2200/16* (2013.01); *B01L 2300/0681* (2013.01); *B01L 2400/0409* (2013.01); *B01L 2400/0487* (2013.01)

(56) References Cited

U.S. PATENT DOCUMENTS

| | | | | |
|---|---|---|---|---|
| 8,534,319 | B2 * | 9/2013 | Bergeron | F16K 99/0063 137/151 |
| 10,001,125 | B2 * | 6/2018 | Paust | F04D 17/10 |
| 10,661,276 | B2 * | 5/2020 | Moura Pires De Andrade Tenreiro | F04B 19/006 |
| 10,773,257 | B2 * | 9/2020 | Paust | B01F 29/15 |
| 10,882,039 | B2 * | 1/2021 | Schwemmer | B01L 3/502715 |
| 10,906,041 | B2 * | 2/2021 | Czilwik | F16K 99/0063 |
| 11,035,497 | B2 * | 6/2021 | Kim | F16K 99/0063 |
| 11,141,728 | B2 * | 10/2021 | Schwarz | B01L 3/50273 |
| 2017/0151559 | A1 | 6/2017 | Da Fonseca et al. | |
| 2017/0354970 | A1 | 12/2017 | Reis et al. | |
| 2018/0280969 | A1 | 10/2018 | Moura Pires De Andrade Tenreiro et al. | |
| 2019/0070607 | A1 | 3/2019 | Czilwik et al. | |
| 2019/0388886 | A1 | 12/2019 | Schwarz et al. | |

FOREIGN PATENT DOCUMENTS

| | | |
|---|---|---|
| DE | 102017204002 A1 | 9/2018 |
| EP | 2219034 B1 | 4/2019 |
| EP | 3114454 B1 | 5/2021 |
| EP | 3389866 B1 | 6/2021 |
| WO | 2020261229 A1 | 12/2020 |

OTHER PUBLICATIONS

Soroori, Salar, et al., "Design and implementation of fuidic micro-pulleys for flow control on centrifugal microfluidic platforms", Microfluid Nanofluid 16, 1117-1129 DOI 10.1007/s10404-013-1277-7, 13 pp.

* cited by examiner

NEGATIVE PRESSURE SWITCHING OF LIQUID

CROSS-REFERENCE TO RELATED APPLICATIONS

This application is a continuation of copending International Application No. PCT/EP2022/071973, filed Aug. 4, 2022, which is incorporated herein by reference in its entirety, and additionally claims priority from German Application No. 10 2021 208 891.0, filed Aug. 13, 2021, which is also incorporated herein by reference in its entirety.

TECHNICAL FIELD

The present invention relates to devices and methods for handling liquids and, in particular, to such devices and methods which allow liquid to be switched from one fluid chamber to another fluid chamber via a flow barrier using negative pressure.

BACKGROUND OF THE INVENTION

Centrifugal microfluidics deals with handling liquids in the picoliter to milliliter range in rotating systems. Such systems are usually disposable polymer cartridges which are used in or instead of centrifuge rotors, with the intention of automating laboratory processes. Standard laboratory processes such as pipetting, centrifugation, mixing or aliquoting can be implemented in a microfluidic cartridge. For this purpose, the cartridges contain channels for fluid guidance and chambers for collecting liquids. In general, such structures designed to handle fluids may be referred to as fluidics structures. In general, such cartridges may be referred to as fluidics modules.

The cartridges can be subjected to a predefined sequence of rotational frequencies, the frequency protocol, so that the liquids in the cartridges can be moved by the centrifugal force. Centrifugal microfluidics is mainly used in laboratory analysis and mobile diagnostics.

For the use of such cartridges and for the implementation of basic operations in a possible product, the robustness and simplicity of handling the processes is of utmost importance. Furthermore, it is advantageous if the basic operations are realized monolithically on the cartridge so that no additional components or materials are entailed, which would significantly increase the cost of the cartridge due to material costs or additional assembly and connection technology.

In particular, switching of liquids is used as a fundamental operation or basic operation for the execution of process chains in order to be able to separate successive fluidic processing steps from one another. Switching processes are therefore indispensable for the automation of laboratory processes in a centrifugal microfluidic rotor.

In the field of centrifugal microfluidics, a processing protocol generally acts on all fluidics structures of a cartridge simultaneously. The increasing integration of successive or parallel processing steps generally results in increasing restrictions for the permissible processing protocols. In order to nevertheless be able to integrate various fluidic operations on a centrifugal microfluidic cartridge, there is need for structures and methods for switching liquids for which the exact conditions for the occurrence of the switching process can be adjusted within a wide range by suitable implementation.

Numerous methods for switching a liquid in centrifugal microfluidic systems are known from conventional technology.

Salar Soroori et al, "Design and implementation of fluidic mirco-pulleys for flow control on centrifugal microfluidic platforms", Microfluid Nanofluid (2014) 16:1117-1129, Springer-Verlag, disclose a method in which a working liquid chamber is connected to a sample liquid chamber via a transfer chamber. The working liquid can be transferred centrifugally from the working liquid chamber into a waste chamber so that a negative pressure is generated in the transfer chamber and a sample liquid is transferred radially inwards from the sample liquid chamber into the transfer chamber by this negative pressure. A working liquid is therefore used here, which is forced radially outwards under the effect of centrifugal forces. The negative pressure forming in the closed fluidic system draws the sample liquid as the target liquid radially inwards via a siphon into the transfer chamber, which is a target chamber.

Robert Gorkin et al, "Suction-enhanced siphon valves for centrifugal microfluidic platforms", Microfluid Nanofluid (2012) 12:345-354, DOI 10.1007/s10404-011-0878-2, Springer-Verlag, disclose a method using negative pressure generated by a liquid flowing past a T-junction to switch a siphon. More specifically, a radially inner chamber is connected to a radially outer chamber via a radially descending channel. A fluid channel, which has a siphon, opens into the radially descending channel. A pressure drop takes place via the radially descending channel, which creates a negative pressure through which liquid can be drawn from the siphon channel into the radially descending channel and thus the radially outer chamber.

DE 10 2016 207 845 A1 discloses a device for handling liquids in which an under pressure is generated by lowering a temperature in a fluid chamber, through which liquid can be drawn into the chamber via a siphon.

The object underlying the invention is providing fluidics modules and methods which enable liquids to be switched in a centrifugal microfluidic system in an advantageous manner and which allow conditions for the switching process to occur to be adjusted within a wide range by means of a suitable implementation.

SUMMARY

According to an embodiment, a method for handling liquid using a fluidics module having: first fluidics structures having a first fluid chamber, second fluidics structures having a second fluid chamber, a first fluidic connection having a fluidic resistance between the first fluid chamber and the second fluid chamber, third fluidics structures having a third fluid chamber, a second fluidic connection between the first fluid chamber and the third fluid chamber, the second fluidic connection having a barrier, the barrier having an inverted siphon, a capillary valve, a geometric valve or a fluid channel, the opening of which into the third fluid chamber is located radially further inwards than its opening into the first fluid chamber, wherein the flow resistance of the first fluidic connection is higher than the flow resistance of the second fluidic connection, a pressure compensation channel between the second fluid chamber and the third fluid chamber, and fourth fluidics structures having a fourth fluid chamber, which is connected to the second fluidics structures via a third fluidic connection, wherein a) the second fluidics structures have a partition wall between a first chamber portion of the second fluid chamber, into which the first fluidic connection opens, and a second chamber portion of the second fluid chamber, into which the third fluidic connection opens, which can be flown over by the liquid in the second fluid chamber due to an Euler force generated by a change in rotational speed of the fluidics module, or b) the third fluidic connection has an inverted siphon, may have the step of: rotating the fluidics module to generate a centrifugal force at which the fluidic resistance of the first fluidic connection is overcome, but not the barrier to transfer liquid centrifugally under rotation from the first fluid chamber through the fluidic resistance of the first fluidic connection into the second fluid chamber, while the barrier of the second fluidic connection initially prevents liquid from passing from the first fluid chamber into the third fluid chamber, wherein, when rotating, at least some of the liquid is transferred from the second fluid chamber via the third fluidic connection into the fourth fluid chamber under rotation by, if feature b) is fulfilled, an apex of the inverted siphon of the third fluidic connection to be wetted completely by the liquid transferred into the second fluid chamber, or, if feature a) is fulfilled, the rotational speed to be changed in order for the liquid transferred into the second fluid chamber to flow over the partition wall in order to generate a negative pressure in the second fluid chamber and the third fluid chamber, which is connected to the second fluid chamber via the pressure compensation channel, and wherein the barrier in the second fluidic connection is overcome by liquid from the first fluid chamber due to the generated negative pressure to transfer liquid from the first fluid chamber to the third fluid chamber via the second fluidic connection while the fluidic resistance of the first fluidic connection prevents liquid from passing by the liquid falling below a certain hydrostatic height in the first fluid chamber, and/or by reducing the rotational speed since the fluidic resistance of the first fluidic connection and the barrier are implemented relative to each other in such a way that the negative pressure in the second fluid chamber and the third fluid chamber draws liquid into the third fluid chamber mainly through the second fluidic connection via the barrier and not into the second fluid chamber via the fluidic resistance.

Examples provide a fluidics module comprising: first fluidics structures having a first fluid chamber; second fluidics structures having a second fluid chamber; a first fluidic connection having a fluidic resistance between the first fluid chamber and the second fluid chamber; third fluidics structures having a third fluid chamber; a second fluidic connection between the first fluid chamber and the third fluid chamber, the second fluidic connection having a barrier; a pressure compensation channel between the second fluid chamber and the third fluid chamber; and fourth fluidics structures having a fourth fluid chamber connected to the second fluidics structures via a third fluidic connection. Liquid can be transferred centrifugally under rotation from the first fluid chamber into the second fluid chamber by the fluidic resistance of the first fluidic connection, while the barrier of the second fluidic connection initially prevents liquid from passing from the first fluid chamber into the third fluid chamber. At least some of the liquid from the second fluid chamber can be transferred under rotation into the fourth fluid chamber via the third fluidic connection in order to generate a negative pressure in the second fluid chamber and the third fluid chamber, which is connected to the second fluid chamber via the pressure compensation channel. The barrier in the second fluidic connection is configured to be overcome by liquid from the first fluid chamber due to the generated negative pressure in order to transfer liquid from the first fluid chamber into the third fluid chamber via the second fluidic connection.

Examples provide a method for handling liquid using a corresponding fluidics module comprising: first fluidics structures having a first fluid chamber; second fluidics structures having a second fluid chamber; a first fluidic connection having a fluidic resistance between the first fluid chamber and the second fluid chamber; third fluidics structures having a third fluid chamber, a second fluidic connection between the first fluid chamber and the third fluid 10 chamber, the second fluidic connection having a barrier, a pressure compensation channel between the second fluid chamber and the third fluid chamber, and fourth fluidics structures having a fourth fluid chamber connected to the second fluidics structures via a third fluidic connection. The method comprises rotating the fluidics module to centrifugally transfer liquid from the first fluid chamber to the second fluid chamber through the first fluidic connection while the barrier of the second fluidic connection initially prevents liquid from passing from the first fluid chamber to the third fluid chamber, and to transfer at least some of the liquid from the second fluid chamber to the fourth fluid chamber via the third fluidic connection in order to generate a negative pressure in the second fluid chamber and the third fluid chamber, which is connected to the second fluid chamber via the pressure compensation channel, liquid from the first fluid chamber overcoming the barrier of the second fluidic connection due to the negative pressure generated and being transferred into the third fluid chamber via the second fluidic connection.

Examples thus provide fluidics modules, devices and methods for selectively switching liquids in centrifugal microfluidic cartridges. It has been recognized that corresponding fluidics modules and methods provide a way of switching liquids which is simultaneously monolithically integrable and easily manufacturable, largely independent of liquid and material properties, and adaptable to a wide range of process conditions.

It has been recognized that this can be achieved by effecting a transfer of some of a liquid across a fluidic resistance (between the first and second fluid chambers) and then using the liquid thus transferred to create a negative pressure. The negative pressure is then used to switch that part of the liquid not transferred via the fluidic resistance over a barrier (in the second fluidic connection). In examples, a first liquid can accordingly be transferred via the fluidic resistance, wherein the negative pressure can then be used to switch a second liquid, different from the first liquid, via the barrier. Examples thus provide switching of a process liquid via a barrier, such as an inverted siphon, using an under pressure generated by the process liquid itself or by a liquid separated therefrom.

BRIEF DESCRIPTION OF THE DRAWINGS

Embodiments of the invention are explained in more detail below with reference to the accompanying drawings, in which.

DETAILED DESCRIPTION OF THE INVENTION

Figure 1:
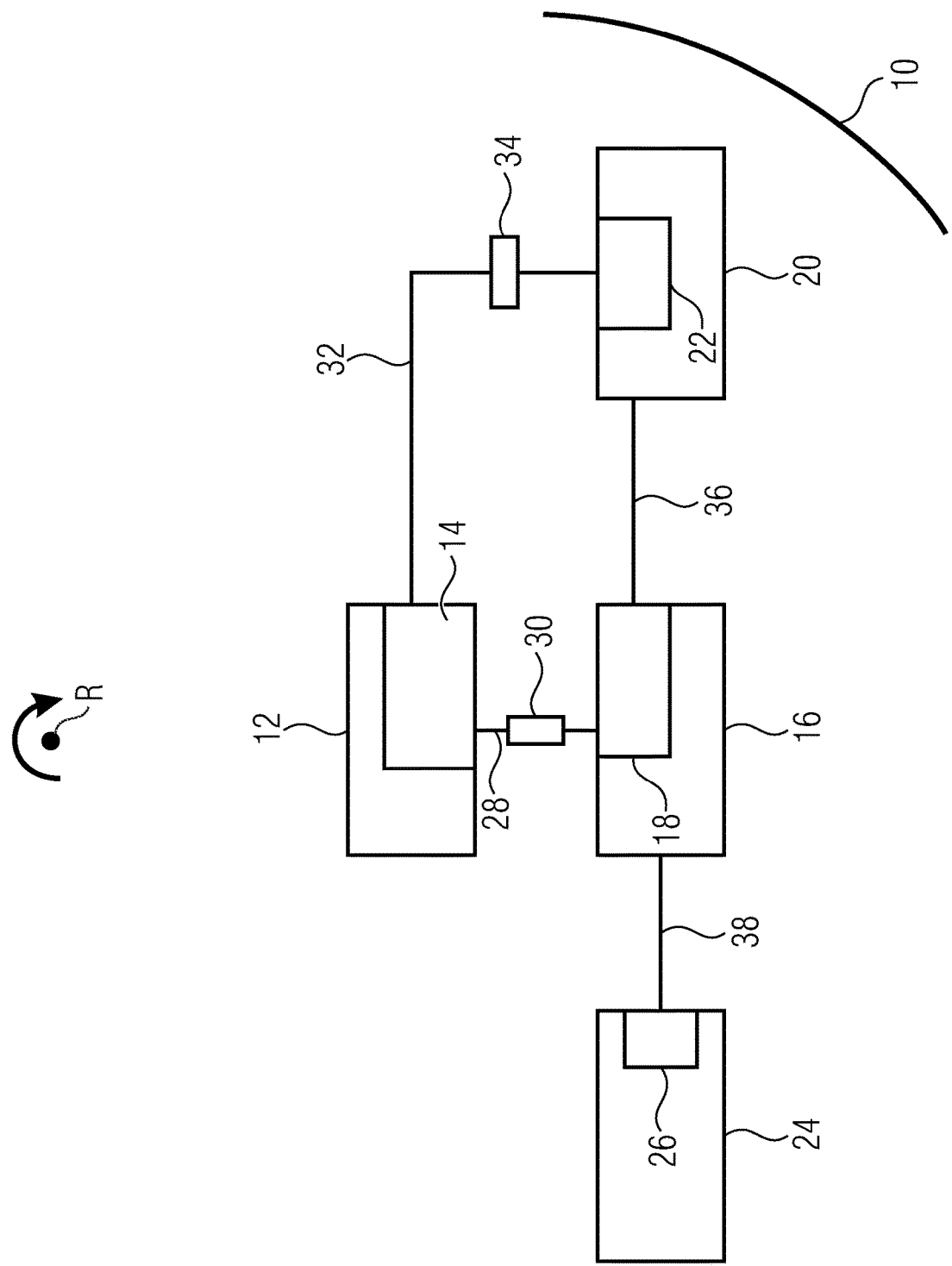
FIG. 1 schematically shows a fluidics module according to an example.

In the following, examples of the present disclosure are described in detail using the accompanying drawings. It should be noted that identical elements or elements having the identical functionality are provided with identical or similar reference numerals, and a repeated description of elements provided with the identical or similar reference numerals is typically omitted. In particular, identical or similar elements may be provided with reference numerals having an identical number with a different or no lower case letter. Descriptions of elements having the identical or similar reference numerals may be interchangeable. In the following description, many details are described in order to provide a more thorough explanation of examples of the disclosure. However, it is apparent to those skilled in the art that other examples may be implemented without these specific details. Features of the various examples described may be combined with one another, unless features of a corresponding combination are mutually exclusive or such a combination is expressly excluded.

Before explaining examples of the present disclosure in more detail, definitions of some terms used herein are provided.

Negative pressure (or underpressure) is defined herein as the pressure difference between the ambient pressure (usually atmospheric pressure: patm ~1013 hPa) and a generated lower pressure (<patm).

A retentate is defined as the liquid or solid components which are retained by the filter membrane during the separation process using a filter membrane.

Permeate is defined as liquid or solid components of a liquid which pass through the membrane during the separation process using a filter membrane.

The term liquid as used herein includes, as is obvious to those skilled in the art, in particular liquids containing solid components, such as suspensions, biological samples and reagents.

An inverted siphon channel is defined herein as a microfluidic channel or section of a microfluidic channel in a fluidics module (a centrifugal microfluidic cartridge) in which the inlet and outlet of the channel have a greater distance from the center of rotation than an intermediate region of the channel. A siphon apex is the area of a siphon channel in a fluidics module with a minimum distance from the center of rotation.

A fluidics module is defined herein as a module, for example a cartridge, having microfluidics structures configured to enable liquid handling as described herein. A centrifugal microfluidic fluidics module (cartridge) is defined as a corresponding module which can be subjected to rotation, for example in the form of a fluidics module insertable into a body of rotation, or a body of rotation.

When the term fluid channel is used herein, it refers to a structure whose length dimension from a fluid inlet to a fluid outlet is greater, for example more than 5 times or more than 10 times greater, than the dimension or dimensions defining the flow cross-section. Thus, a fluid channel has a flow resistance for passing the same from the fluid inlet to the fluid outlet. A fluid chamber, on the other hand, is a chamber with dimensions such that the flow through the chamber has a negligible flow resistance compared to connected channels, which can be, for example, $\frac{1}{100}$ or $\frac{1}{1000}$ of the flow resistance of the channel structure, connected to the chamber, with the lowest flow resistance.

Examples of the invention can be used in particular in the field of centrifugal microfluidics, which involves the processing of liquids in the picoliter to milliliter range. Accordingly, the fluidic structures can have suitable dimensions in the micrometer range for handling corresponding liquid volumes.

If the term radial is used here, this means radial with respect to the center of rotation around which the fluidics module or the rotational body is rotatable. In the centrifugal field, a radial direction away from the center of rotation is therefore radially decreasing and a radial direction towards the center of rotation is radially increasing. A fluid channel the beginning of which is closer to the center of rotation than its end, is therefore radially decreasing, while a fluid channel whose beginning is further away from the center of rotation than its end is radially increasing. A channel having a radially increasing section therefore has directional components which increase radially or run radially inwards. It is clear that such a channel does not have to run exactly along a radial line, but can run at an angle to the radial line or be curved.

Unless otherwise stated herein, room temperature (20° C.) is to be assumed for temperature-dependent variables.

Examples of the present disclosure provide microfluidic structures and methods in a centrifugal microfluidic system for centrifugal-pneumatic switching of liquids. FIG. 1 shows an example of fluidics structures formed in a fluidics module 10 and configured to at least partially implement the functionalities described herein. The fluidics module 10 is rotatable about a center of rotation or center of revolution R and may be implemented as a body of rotation or as a module insertable into a body of rotation. The fluidics module 10 has first fluidics structures 12 having a first fluid chamber 14, second fluidics structures 16 having a second fluid chamber 18, third fluidics structures 20 having a third fluid chamber 22, and fourth fluidics structures 24 having a fourth fluid chamber 26. The first to fourth fluidics structures may each have additional fluid chambers, as long as this does not impair the functionalities described herein. In examples, the first to fourth fluidics structures may each have a number of chambers, wherein in examples the number is one. The fluid chamber or fluid chambers of the first fluidics structures may be liquid reservoirs or reaction chambers.

The first fluid chamber 14 is fluidically connected to the second fluid chamber 18 via a first fluidic connection 28, which has a fluidic resistance 30. The first fluid chamber 14 is further fluidically connected to the third fluid chamber 22 via a second fluidic connection 32, which has a barrier 34. The second fluid chamber 18 is further fluidically connected to the third fluid chamber 22 via a pressure compensation channel 36. The fourth fluid chamber 26 is fluidically connected to the second fluidics structures 16 via a third fluidic connection 38.

Liquid can be transferred centrifugally under rotation from the first fluid chamber 14 through the fluidic resistance 30 of the first fluidic connection 28 into the second fluid chamber 18, while the barrier 34 of the second fluidic connection 32 initially prevents liquid from passing from the first fluid chamber 14 into the third fluid chamber 22. The fluidic resistance 30 and the barrier 34 can be configured such that the fluidics module 10 can be subjected to a rotation which generates a centrifugal force in which the fluidic resistance 30 is overcome, but not the barrier 34.

At least some of the liquid from the second fluid chamber 18 is transferable under rotation into the fourth fluid chamber 26 via the third fluidic connection 38 to create a negative pressure in the second fluid chamber 18 and the third fluid chamber 22, which is connected to the second fluid chamber 18 via the pressure compensation channel. The fluidics structures are configured to enable the generation of the negative pressure. In examples, the fluidic resistance of the first fluidic connection 28 and/or liquid remaining in the first fluid chamber 14 can prevent air from escaping via the first fluidic connection 28. The fluidics structures and the barrier 34 in the second fluidic connection 32 are configured such that liquid from the first fluid chamber 14 can overcome the barrier 34 due to the generated negative pressure so that liquid can be transferred from the first fluid chamber 14 via the second fluidic connection 32 into the third fluid chamber 22, while the fluidic resistance 30 of the first fluidic connection prevents a significant amount of liquid from entering the second fluid chamber 18 via the first fluidic connection 28. The fluidic resistance 30 and the barrier 34 are implemented relative to each other in such a way that the negative pressure in the second fluid chamber and the third fluid chamber draws liquid into the third fluid chamber 22 mainly through the second fluidic connection 32 via the barrier 34 and not into the second fluid chamber 18 via the fluidic resistance 30. This can be achieved, for example, by implementing the fluidic resistance 30 such that, at a given rotational speed, it prevents the liquid from passing when the liquid falls below a certain hydrostatic height in the first fluid chamber 14. Alternatively or additionally, this can be achieved by reducing the rotational speed.

Examples thus allow some of the liquid to be initially transferred from the first fluid chamber 14 to the second fluid chamber 18 via the first fluidic connection 28, whereupon another portion of the liquid can be transferred from the first fluid chamber 14 to the third fluid chamber 22 via the second fluidic connection 32. In examples, a first liquid may also first be transferred completely into the second fluid chamber 18 via the first fluidic connection 28, whereupon a second liquid different from the first fluid, which is introduced into the first fluid chamber after the first liquid has been transferred, may be transferred into the third fluid chamber 22 via the second fluidic connection 32. Thus, to generate the negative pressure in the second fluid chamber 18 and the third fluid chamber 22, a process fluid itself or a liquid introduced into the first fluid chamber 14 before the process fluid can be used.

In examples, the barrier 34 of the second fluidic connection 32 may comprise an inverted siphon. In such examples, the fluidics module may initially be rotated at a rotational speed at which the centrifugal force is sufficient to overcome the fluidic resistance 30 while preventing the liquid to pass through the siphon from the first fluid chamber 14. The negative pressure present in the third fluid chamber 22 can then generate a force which exceeds the centrifugal force, allowing liquid from the first fluid chamber 14 to pass through the siphon. This can be further assisted by reducing the rotational speed.

In examples, the barrier 34 has a capillary valve or a geometric valve which, without the negative pressure, initially prevents liquid from passing through the second fluidic connection 32 and can be overcome by the negative pressure present in the third fluid chamber 22. In microfluidics, a capillary valve represents a barrier for flow-through of a liquid, in which a meniscus of the liquid forms on the valve such that capillary forces counteract movement of the liquid through the valve. If a critical pressure difference is applied across the valve, the capillary forces are overcome, the liquid passes through the valve and the valve is switched to flow. A capillary valve can be realized as a geometric valve by a hydrophobic coating or by a special geometric structure. A geometric valve is usually an abrupt widening of a microfluidics channel which contains the sharpest edge possible in at least one direction of the widening, at which the meniscus is pinned.

In examples, the barrier has a radially ascending fluid channel whose opening into the third fluid chamber 22 is located radially further inwards than its opening into the first fluid chamber 14. Such a radially ascending fluid channel can be overcome by the negative pressure present in the third fluid chamber 22.

In examples, the third fluidic connection 38 has an inverted siphon whose apex is wettable by liquid in the second fluidics structures 16 reaching a certain filling level, i.e. the pressure acting on the liquid in the second fluid chamber 18 is sufficient to wet the siphon against the centrifugal force. Thus, complete "priming" (wetting) of the siphon can be achieved and the liquid can be transferred from the second fluid chamber 18 to the fourth fluid chamber 26.

In examples, the second fluidics structures 16 have a partition wall between a first chamber section of the second fluidic chamber, into which the first fluidic connection opens, and a second chamber section of the second fluidic chamber, into which the third fluidic connection opens, which can be overflowed by the liquid in the second fluidic chamber due to an Euler force resulting from a change in a rotational speed of the fluidics module. The partition wall protrudes into the second fluidics structures 16 from a radially outer position to a radially inner position. The partition wall may have an inclined wall portion which extends from a radially outer region of the first chamber section in a radially ascending direction towards the second chamber section.

In examples, the second fluid chamber is ventilated via the third fluidic connection and the fourth fluid chamber in an initial state in which there is no liquid in it. By transferring the liquid from the second fluid chamber to the fourth fluid chamber, this ventilation can be closed so that a negative pressure can be generated in the second and third fluid chambers.

In examples, the first fluidic connection has a fluid channel with a flow cross-section of less than 40000 µm². In examples, the fluidic resistance of the first fluidic connection can be formed by a resistance channel with a diameter of at most 100 µm. A flow resistance having such a flow cross-section can be overcome at a rotational speed at which the barrier 34 prevents liquid from passing through the second fluidic connection 32 into the second fluid chamber 22.

In examples, the first fluidic connection has a filter membrane and a further fluid chamber, which is separated from the first fluid chamber by the filter membrane. The filter membrane may form the fluidic resistance or may be provided in addition to a further fluidic resistance.

Such examples allow process liquid to be initially passed from the first fluid chamber 14 through the filter membrane into the second fluid chamber 18 so that retentate is retained by the filter membrane. The permeate can then be transferred from the second fluid chamber 18 to the fourth fluid chamber 26, while the retentate can be transferred to the third fluid chamber 22 via the second fluidic connection 32.

In examples, a biomolecule- or cell-binding matrix may be disposed in the first fluid chamber. Such examples allow biomolecules, such as nucleic acids, proteins, hormones, etc., or cells, such as bacteria, human cells, animal cells, etc., to be bound in the first fluid chamber. The biomolecules or cells bound in this way can then be transferred via the second fluidic connection 32 into the third fluidic chamber 22, for example using a suitable elution solution.

Examples of the present disclosure provide a device for handling liquids, comprising any fluidics module as described herein, and drive means for imparting rotation to the fluidics module. The drive means may comprise a controller to effect rotation of the fluidics module to achieve all or part of the functionalities described herein. The device may be configured to implement methods as described herein. The drive means may be configured to rotate the fluidics module 10 to centrifugally transfer liquid from the first fluid chamber 14 through the first fluidic connection 30 into the second fluid chamber 18, while the barrier 34 of the second fluidic connection 32 initially prevents liquid from passing from the first fluid chamber 14 into the third fluid chamber 22. By rotating the fluidics module, at least some of the liquid can be transferred from the second fluid chamber 18 to the fourth fluid chamber 26 via the third fluidic connection 38 to create a negative pressure in the second fluid chamber 18 and thus also the third fluid chamber 22, which is connected to the second fluid chamber 18 via the pressure compensation channel 36. Due to the generated negative pressure, the barrier 34 is overcome and liquid from the first fluid chamber 14 reaches the third fluid chamber 22 via the second fluidic connection 32.

In examples, rotating the fluidics module may include rotating at a first rotational speed to transfer the liquid from the first fluid chamber 14 to the second fluid chamber 18 and rotating at a second rotational speed different from the first rotational speed to transfer the liquid from the first fluid chamber to the third fluid chamber due to the negative pressure generated. Depending on the configuration of the first fluidic resistance and the barrier, the second rotational speed may be lower or higher than the first rotational speed.

In examples, depending on the hydrostatic height in the first fluid chamber 14, there is hardly any transfer across the fluidic resistance 30 into the second fluid chamber, even if the rotational speed remains the same. In examples, the rotation for transferring the liquid from the first fluid chamber 14 into the second fluid chamber 18 and for generating the negative pressure can therefore take place at the same rotational speed. In examples, transferring at least some of the liquid from the second fluid chamber to the fourth fluid chamber may also take place at the same rotational speed, for example when the third fluidic connection 38 comprises an inverted siphon whose apex is completely wetted by the liquid transferred to the second fluid chamber 18. In examples in which the second fluidics structures comprise a partition wall between the second fluidic chamber and the third fluidic connection, rotating may comprise changing the rotational speed to cause the liquid in the second fluidic chamber to flow over the partition wall due to an Euler force and be switched into the fourth fluid chamber. The partition wall can be regarded as an inertia switch, wherein the rotational speed can be changed to a higher frequency for the transfer across the partition wall, for example.

In examples in which the first fluidic connection comprises a filter membrane, rotating can be performed to transfer a permeate passing through the filter membrane into the second fluid chamber and to transfer a retentate retained by the membrane with the liquid due to the generated negative pressure, from the first fluid chamber via the second fluidic connection into the third fluid chamber. Such examples enable the purification of biomolecules, particles or cells.

Examples of the present disclosure provide a method of introducing a sample liquid into the first fluid chamber 14, wherein the first fluid chamber 14 comprises a biomolecule- or cell-binding matrix to bind biomolecules (nucleic acids, proteins, hormones, etc.) or cells (bacteria, human cells, animal cells, etc.) to the matrix. Rotation of the fluidics module is performed to transfer the sample liquid from the first fluid chamber 14 to the second fluid chamber 18. A wash solution is introduced into the first fluid chamber 14 to remove contaminants. Rotation is performed to transfer the wash solution from the first fluid chamber 14 to the second fluid chamber 18. An elution solution or lysis reagent is introduced into the first fluid chamber 14 to elute the purified biomolecules or to lyse cells and to produce an eluate or a lysate. Rotation is performed to transfer the wash solution and the sample solution at least partially from the second fluid chamber 18 to the fourth fluid chamber 26 to create the negative pressure and thereby transfer the eluate or lysate from the first fluid chamber 14 to the third fluid chamber 22.

In examples, liquid is thus driven by means of centrifugal force from a first chamber 14 via a fluidic resistance 30, for example a channel or a filter membrane, into a second chamber 18 located radially further out. The first chamber 14 is additionally connected to a further chamber 22 via a barrier 34, for example a siphon-shaped fluidic path. Liquid in the first fluid chamber 14 is at least partially transferred to the second fluid chamber 18 where it is used to generate a negative pressure. This negative pressure is used to switch the remaining liquid in the first fluid chamber 14, or another liquid introduced into the first fluid chamber 14, into a further fluid chamber 22 via the barrier 34, for example the siphon-shaped fluidic path. One possible application is filtration in which the permeate is used to generate the negative pressure and the retentate, in which target particles are present, is transferred to a further chamber. In examples, one possible application is nucleic acid purification by means of a so-called bind-wash-elute process, in which the eluate is switched to a target chamber at the end of the purification process with the aid of the negative pressure.

In the following, specific examples of fluidics modules are described with reference to FIGS. 2A to 4C, which show respective fluidics structures of such fluidics modules in plan view.

Figure 2A:
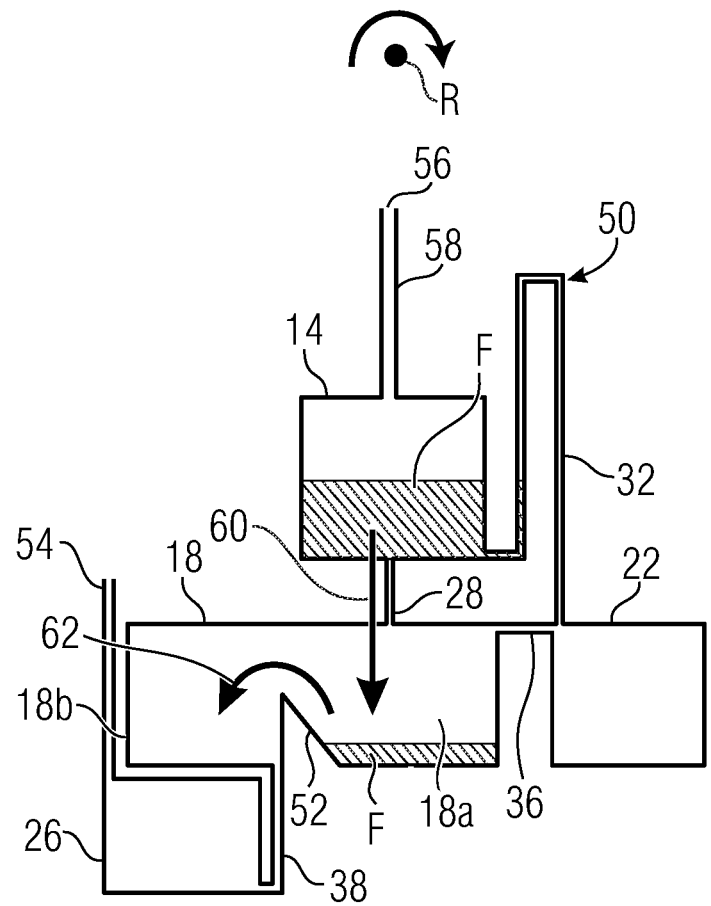
FIGS. 2A to 2C schematically show a fluidics module according to an example with a partition wall between the second fluid chamber and the third fluidic connection.
Figure 2B:
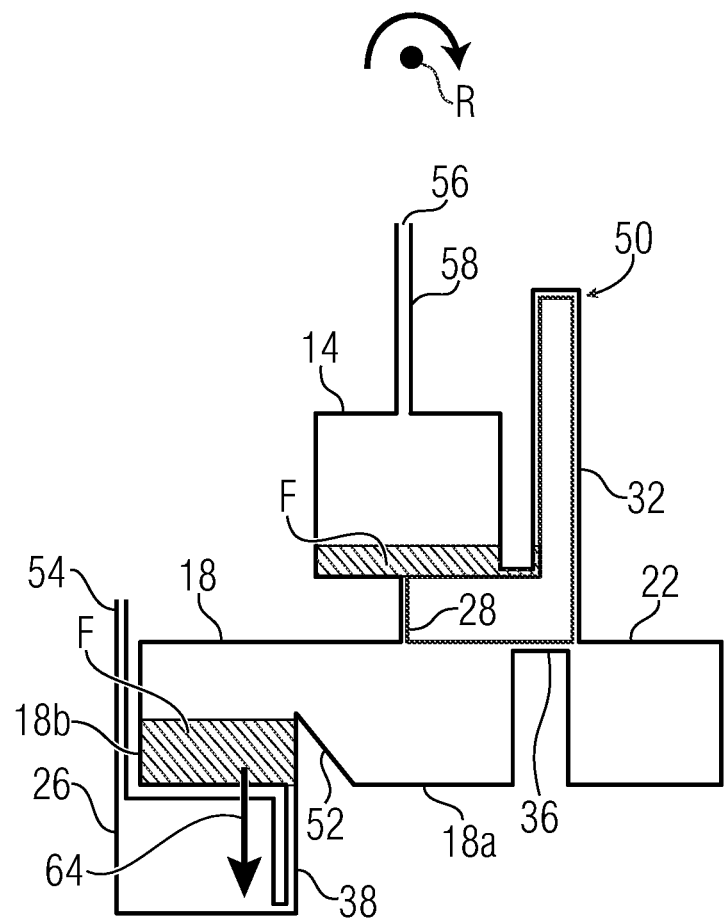
Figure 2C:
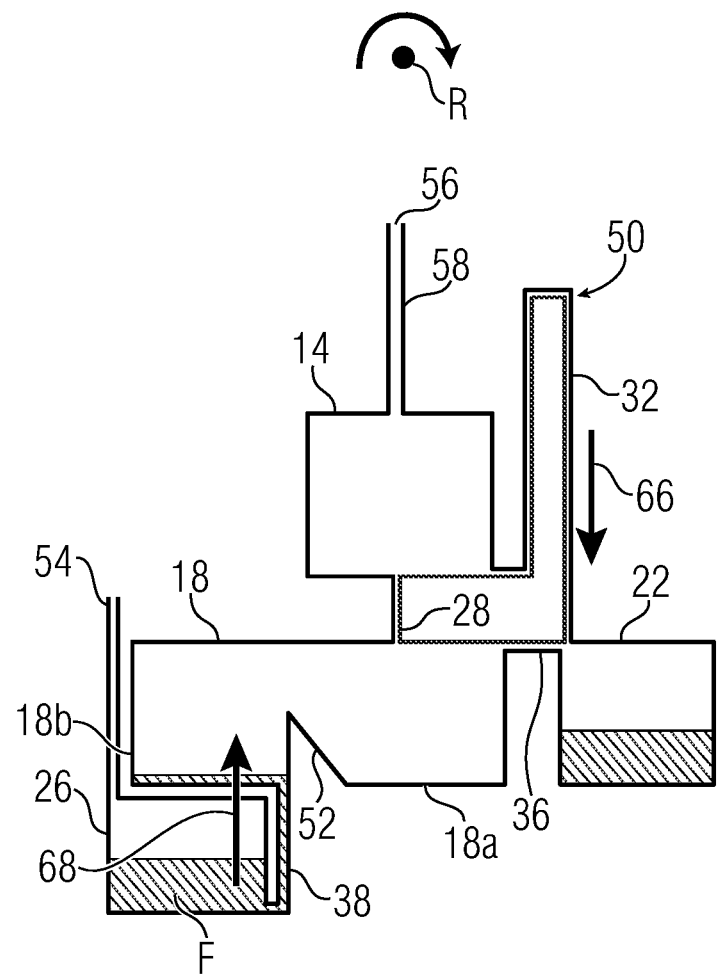

FIGS. 2A to 2C show an example of a fluidics module in which the fluidic resistance of the first fluidic connection is formed by a fluid channel with a small flow cross-section, the barrier is formed by an inverted siphon, and the second fluidics structures have a partition wall. The microfluidic structures of the fluidics module have the first fluid chamber 14, which is connected to the second fluid chamber 18, which is located radially further out, via the first fluidic connection 28 with the fluidic resistance. The first fluid chamber 14 is additionally connected to the third fluid chamber 22 via the second fluidic connection 32, which has an inverted siphon 50 as a barrier. The liquid is transferred through the inverted siphon 50 during switching. The third fluid chamber 22 is connected to the second fluid chamber 18 via the pressure compensation channel 36, which is an air-conducting channel. The second fluid chamber 18 has a partition wall 52 in the form of a ramp-shaped structure, which divides the second fluid chamber 18 into a first chamber section 18a and a second chamber section 18b. The partition 52 projects radially inwardly from a radially outer end of the second fluid chamber 18 with respect to the center of rotation R and has a ramp which extends obliquely radially inwardly toward the second chamber section 18*b*. The first fluidic connection 28 opens into the first chamber section 18*a*. The second chamber section 18*b* of the second fluid chamber 18 is connected via the third fluidic connection 38, which may be implemented by a fluidic resistance channel, to the fourth fluid chamber 26 located radially further outwards. The fourth fluid chamber 26 is vented, as shown schematically by a vent 54. The first fluid chamber is also vented via a filling opening 56 and a filling channel 58. The remaining structures have no ventilation or at least no ventilation to prevent the described functionalities.

In the example shown, the second fluidic connection 32 in the form of a liquid channel having the inverted siphon 50 opens into a radially outer portion of the first fluid chamber 14 and a radially inner portion of the third fluid chamber 22. The first fluidic connection 28 in the form of the resistance channel connects a radially outer portion of the first fluid chamber 14 to a radially inner portion of the first chamber section 18*a* of the second fluid chamber 18. The third fluidic connection 38 in the form of a fluid channel connects a radially outer portion of the second chamber portion 18*b* of the second fluid chamber 18 to a radially outer portion of the fourth fluid chamber 26. The first fluidic connection 28 has a flow cross-section which is much smaller than a flow cross-section of the fluid channel forming the second fluidic connection 32 such that the first fluidic connection 28 provides a high flow resistance for the liquid in the first fluid chamber 14, while the second fluidic connection 32 provides a low flow resistance for the corresponding liquid. The fluid channel of the third fluidic connection 38 may provide a flow resistance which is between the high flow resistance and the low flow resistance.

FIG. 2A shows the corresponding fluidics structures in a state in some of a liquid F has been transferred from the first fluid chamber 14 to the second fluid chamber 18 via the fluidic connection 28, as indicated by an arrow 60 in FIG. 2A. In examples, this may be accomplished by rotating at a first rotational speed driving liquid from the first fluid chamber 14 by high centrifugal forces via the resistance channel 28 into the second fluid chamber 18 which is vented via the third fluidic connection and the fourth fluid chamber 26.

At a certain point in time, for example after a certain portion of the liquid has been transferred from the first fluid chamber 14 to the second fluid chamber 18, liquid is transferred from the second fluid chamber 18 to the second chamber section 18*b* of the second fluid chamber 18 by means of inertia to overcome the ramp-shaped partition wall 52, as indicated by an arrow 62 in FIG. 2A. The resulting state is shown in FIG. 2B, where the liquid is disposed in the second chamber section 18*b*. As a result, the liquid closes the third fluidic connection 38 so that the second fluid chamber 18 and the third fluid chamber 22 connected thereto via the air-conducting pressure compensation channel 36 are no longer vented. If the liquid in the second chamber section 18*b* is now driven by centrifugal forces into the radially outer fourth chamber 26 via the third fluidic connection 38, arrow 64 in FIG. 2B, a negative pressure is generated in the chambers 18 and 22. At rotational speeds at which the force caused by this negative pressure exceeds the centrifugal force acting in the radially ascending channel section of the siphon 50, the negative pressure causes the remaining liquid from the first fluid chamber 14 to wet the inverted siphon 50 and the liquid to be transferred into the third fluid chamber 22 via the second fluidic connection 32. In examples, the rotational speed can be reduced so that the centrifugal force is no longer sufficient to transfer liquid from the first fluid chamber 14 to the second fluid chamber 18 via the first fluidic connection. FIG. 2C shows the resulting state in which the liquid has been transferred from the first fluid chamber 14 into the third fluid chamber 22, as indicated by an arrow 66. Due to the negative pressure present in the second fluid chamber 18, some of the liquid can be transferred back from the fourth fluid chamber 26 into the second fluid chamber 18, as indicated by an arrow 68 in FIG. 2C, but this is irrelevant for the desired functionality.

In examples, rotation of the fluidics module having the fluidics structures shown in FIGS. 2A to 2C may initially occur at a first rotational speed at which some of the liquid is transferred from the first fluid chamber 14 to the second fluid chamber 18. After that, the rotational speed may be changed to transfer the liquid from the first chamber section 18*a* to the second chamber section 18*b* by means of inertia, for example by accelerating or decelerating the fluidics module. The transfer of the liquid from the second fluid chamber 18 to the fourth fluid chamber 26 can then take place at a second rotational speed which is lower than the first rotational speed so that liquid enters the fourth fluid chamber via the third fluidic connection 38 and no more liquid enters the second fluid chamber 18 from the first fluid chamber 14 via the first fluidic connection 28. The resulting negative pressure may be sufficient to draw liquid from the first fluid chamber 14 into the third fluid chamber 22 via the siphon 50. In examples, the rotational speed may be reduced to a third rotational speed which is smaller than the second rotational speed to prime the inverted siphon. Thus, in examples, a high rotational speed may be used to transfer liquid across the first fluidic connection 28, a medium rotational speed may be used to transfer liquid across the third fluidic connection 38, and a low rotational speed may be used while transferring liquid across the second fluidic connection 32.

Figure 3A:
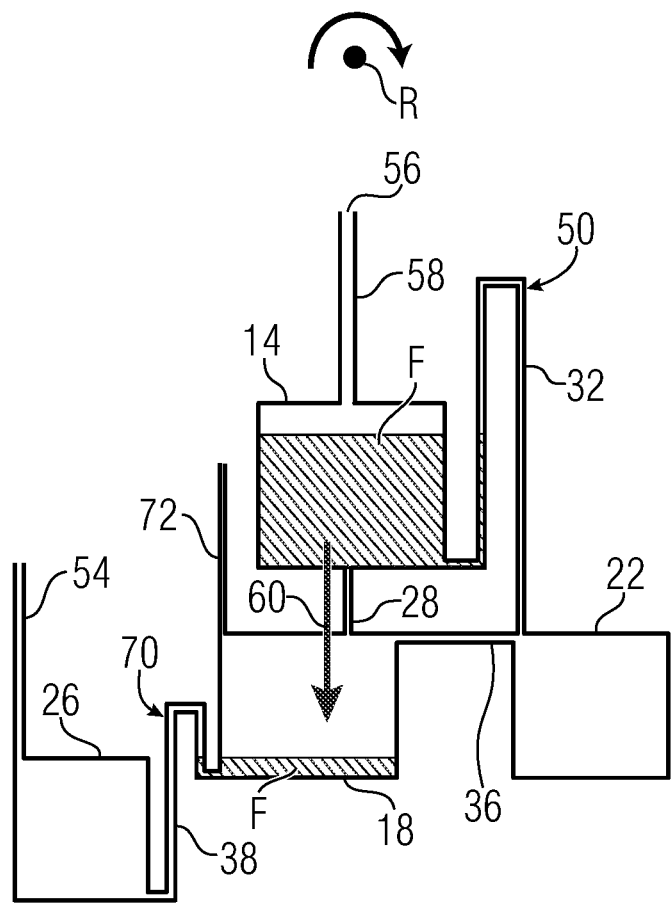
FIGS. 3A to 3C schematically show a fluidics module according to an example in which the third fluidic connection has an inverted siphon.
Figure 3B:
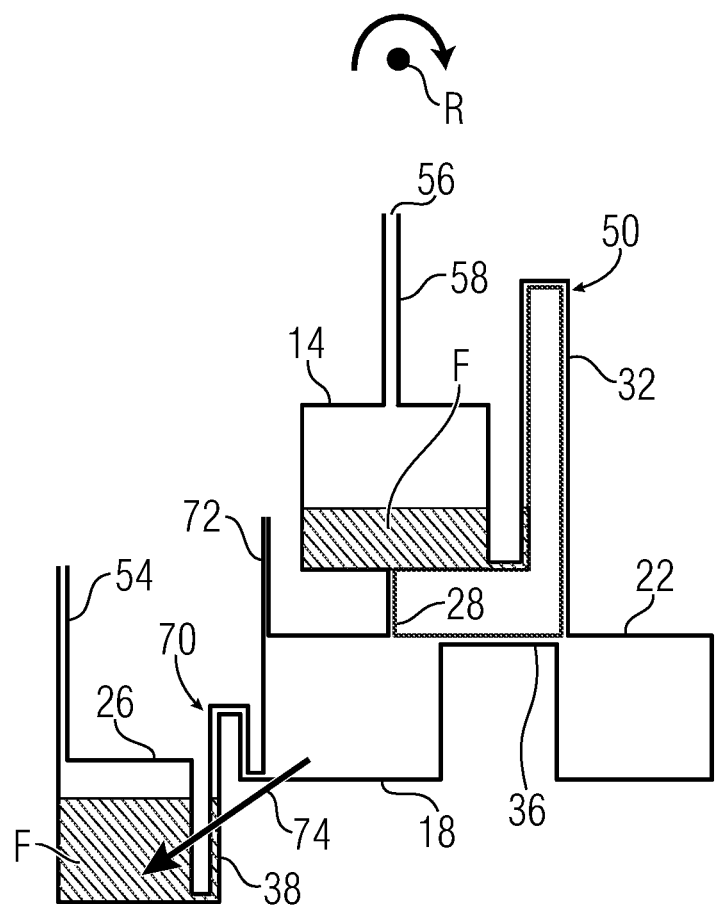
Figure 3C:
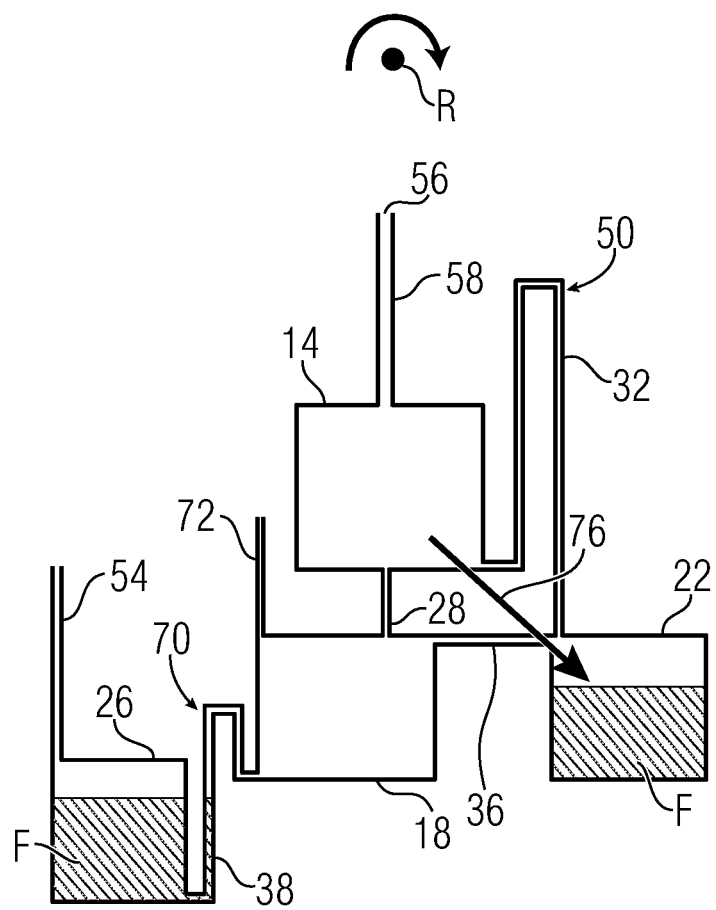

With reference to FIGS. 3A to 3C, a further example of a fluidics module is described below, which differs from the example shown in FIGS. 2A to 2C with regard to the second fluid chamber and the third fluidic connection. In this respect, in particular the differences are discussed below, while the other elements correspond to the elements described with reference to FIGS. 2A to 2C so that a repeated description of the same is omitted. In the example shown in FIGS. 3A to 3B, the second fluidics structures comprise the second fluid chamber 18 and the third fluidic connection 38 comprises an inverted siphon 70. A radially outer portion of the second fluid chamber 18 is connected to a radially outer portion of the fourth fluid chamber 26 via the inverted siphon 70. The second fluid chamber 18 is vented via an air-conducting resistance channel 72. The siphon 70 is configured to allow a transfer of liquid from the second fluid chamber 18 to the fourth fluid chamber 26 when a certain event occurs. The event may be, for example, reaching a certain fill level in the second fluid chamber 2. Alternatively, the event may include a decrease in rotational speed such that the siphon 70 is wetted by capillary forces which outweigh the centrifugal force. In operation, as shown in FIG. 3A, some of the fluid is at first driven from the first fluid chamber through the resistance channel of the first fluidic connection 28 into the second fluid chamber 18. Excess air is discharged via the air-conducting resistance channel 72. At a certain fill level in the second fluid chamber 18, the apex of the siphon 70 is wetted and the liquid is switched into the fourth fluid chamber 26 via the siphon 70 of the third fluidic connection 38, arrow 74 in FIG. 3B. This creates a negative pressure in the chambers 18 and 22. For this purpose, the air-conducting resistance channel has a sufficiently large air resistance. This negative pressure causes the remaining liquid from the first fluid chamber 14 to wet the siphon 50 and the liquid is transferred from the first fluid chamber 14 via the second fluidic connection 32 into the third fluid chamber 22, arrow 76 in FIG. 3C.

In the example shown in FIGS. 3A to 3C, too, a high rotational speed may be used to transfer the liquid via the first fluidic connection, a second rotational speed lower than the first rotational speed may be used to transfer the liquid via the third fluidic connection, and a third rotational speed lower than the second rotational speed may be used to transfer the liquid via the second fluidic connection.

An application example for the structures described with reference to FIGS. 2A to 3C can be, for example, nucleic acid purification by means of a so-called bind-wash-elute process. In this case, a nucleic acid-binding matrix, for example beads or a silica mesh, may be placed upstream in the first fluid chamber 14. The sample can be rinsed through the first fluid chamber 14 so that the nucleic acids bind to the matrix. Wash solutions can then be rinsed through the first fluid chamber 14 to remove impurities. An elution solution can then be added to the first fluid chamber 14 to elute the purified nucleic acids. The previously used solutions can then be used to generate the negative pressure to transfer the eluate of the elution solution into the third fluid chamber 22.

Figure 4A:
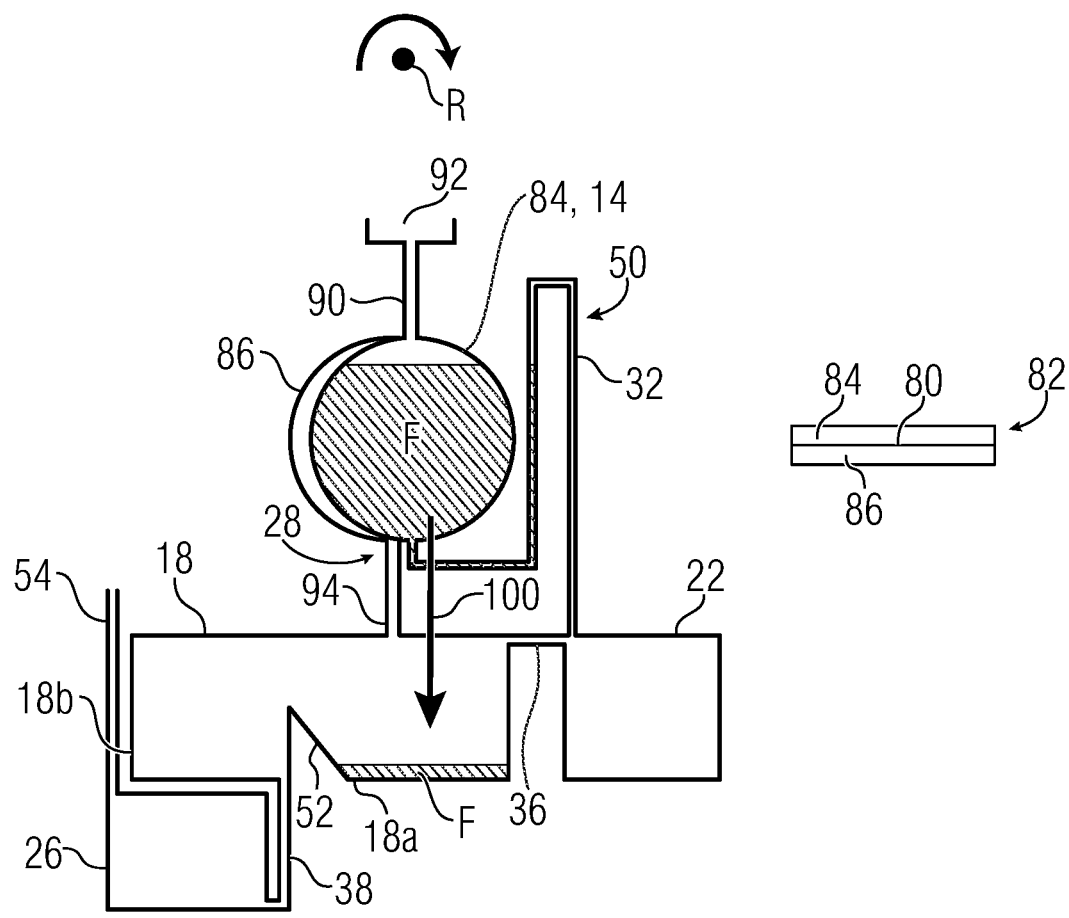
FIGS. 4A to 4C schematically show a fluidics module according to an example in which the fluidic resistance is formed by a membrane.
Figure 4B:
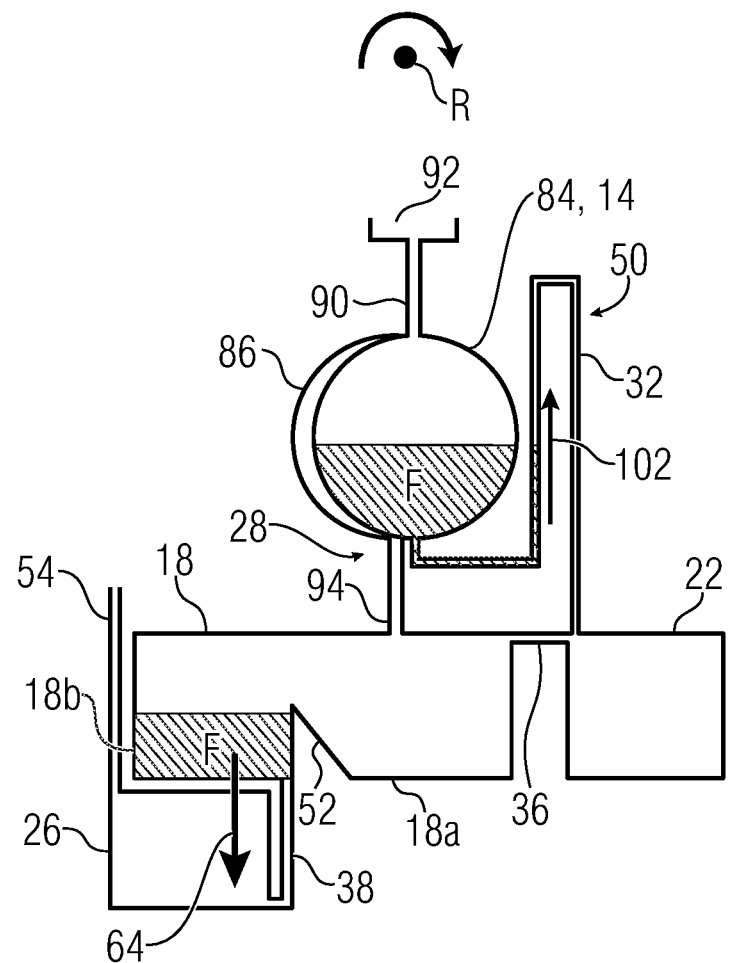
Figure 4C:
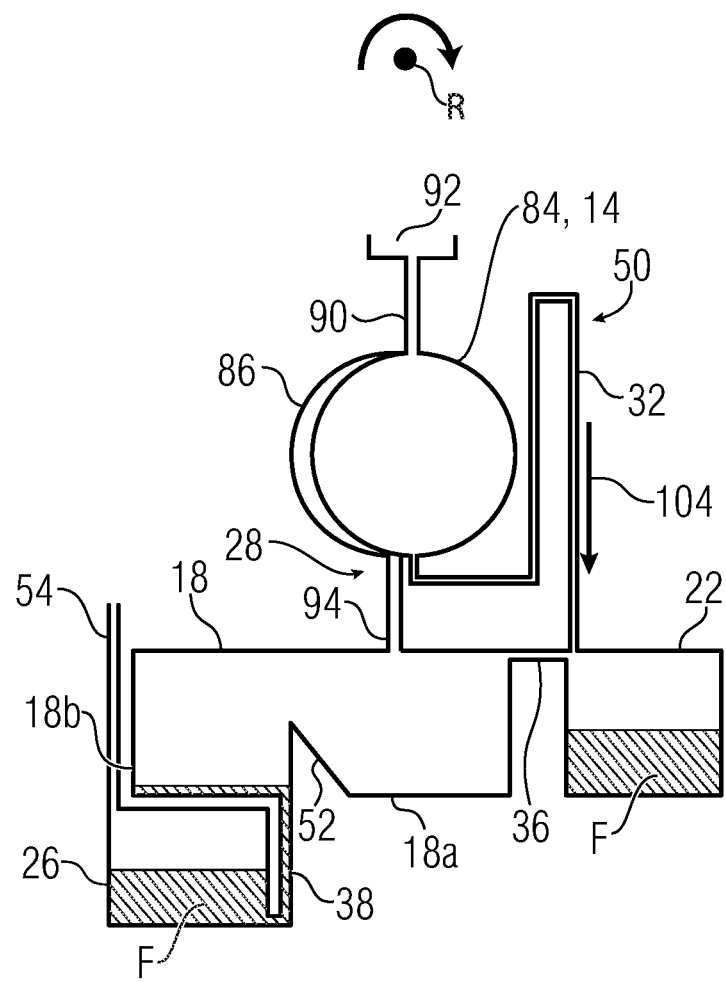

Referring to FIGS. 4A to 4C, a further example of a fluidics module according to the present disclosure is described below, again referring only to differences relative to the example shown in FIGS. 2A to 2C, while a description of the remaining parts is omitted. The example shown in FIGS. 4A to 4C differs from the example shown in FIGS. 2A to 2C in the structure of the first fluid chamber and the first fluidic connection. In the example shown in FIGS. 4A to 4C, an inlet chamber is a filter chamber with a filter membrane. FIG. 4A schematically shows in the right part thereof a cross-section of a filter chamber with a filter membrane 80, which divides a filter chamber 82 into an inlet-side (upper) chamber 84 and an outlet-side (lower) chamber 86. In the left part of FIG. 4A and FIGS. 4B and 4C, the inlet-side chamber 84 and the outlet-side chamber 86 are shown offset from each other for reasons of illustration, although in reality the inlet-side chamber 84 and the outlet-side chamber 86 may overlap completely. The inlet-side chamber 84 represents the first fluid chamber 14 of the fluidics module. The inlet-side chamber 84 may be connected to a fill opening 92 via a fill channel 90 at a radially inner portion. The inlet-side chamber 84 is further fluidically connected to the third fluid chamber 22 via the second fluidic connection 32. In this example, the first fluidic connection 28 has the filter membrane 80, the outlet-side chamber 86 and a fluid channel 94, which fluidically connects a radially outer portion of the outlet-side chamber 86 to a radially inner portion of the second fluid chamber 2. In this example, the filter membrane 80 may form the fluidic resistance of the first fluidic connection 28. In examples, the filter membrane 80 and the fluid channel 94 may together form the fluidic resistance of the first fluidic connection 28.

In operation, liquid is forced by centrifugal forces across the fluidic resistance of the filter membrane 80 through the outlet-side chamber 86 and the fluid channel 94 into the second fluid chamber 18, as shown by an arrow 100 in FIG. 4A. Subsequently, as in the example shown in FIGS. 2A to 2C, the liquid is transferred from the first chamber section 18a of the second fluid chamber 18 into the second chamber section 18b of the second fluid chamber 18. Once a certain volume of the liquid has been filtered, the permeate is used to generate the negative pressure by transferring it from the second chamber portion 18b of the second fluid chamber 18 via the third fluidic connection 38 into the fourth fluid chamber 26, see arrow 64 in FIG. 4B. The siphon 50 of the second fluidic connection 32 is wetted (primed) by the negative pressure, arrow 102. Subsequently, the remainder of the liquid is transferred from the first fluid chamber 84, 14 via the second fluidic connection 32 into the third fluid chamber 22, arrow 104.

In the fluidics module shown in FIGS. 4A to 4C, the filter membrane in particular acts as a fluidic resistance. Even if the remaining liquid in the filter chamber 82 does not fill the entire chamber, the filter membrane 80 is still wetted with liquid and thus represents a high resistance for air so that the negative pressure between the first fluid chamber 14, 84 and the second fluid chamber 18 cannot be compensated via the filter. The negative pressure therefore results in the filter retentate being transferred to the third fluid chamber 22 via the siphon 50 of the second fluidic connection 32.

One possible application of the example shown in FIGS. 4A to 4B is the filtration of a liquid with the aim of concentrating and cleaning particles from the liquid. The liquid and any washing solutions can be pressed through the filter membrane. Some of the liquid with the retained particles remains on the filter. The permeate can then be used to create a negative pressure to transfer the retentate into the target chamber 22.

No separate explanation is needed in that a different combination of features of the described embodiments is possible. For example, in the example shown in FIGS. 4A to 4C, the second fluid chamber 18 and the third fluidic connection 38 could be formed in accordance with the example shown in FIGS. 3A to 3B.

In the example shown in FIGS. 4A to 4C, too, a first rotational speed may be used in the first phase in which liquid is transferred via the first fluidic connection, a second rotational speed which is lower than the first rotational speed may be used in the second phase in which liquid is transferred via the third fluidic connection, and a third rotational speed which is lower than the second rotational speed may be used in the third phase in which liquid is transferred via the second fluidic connection.

Figure 5A:
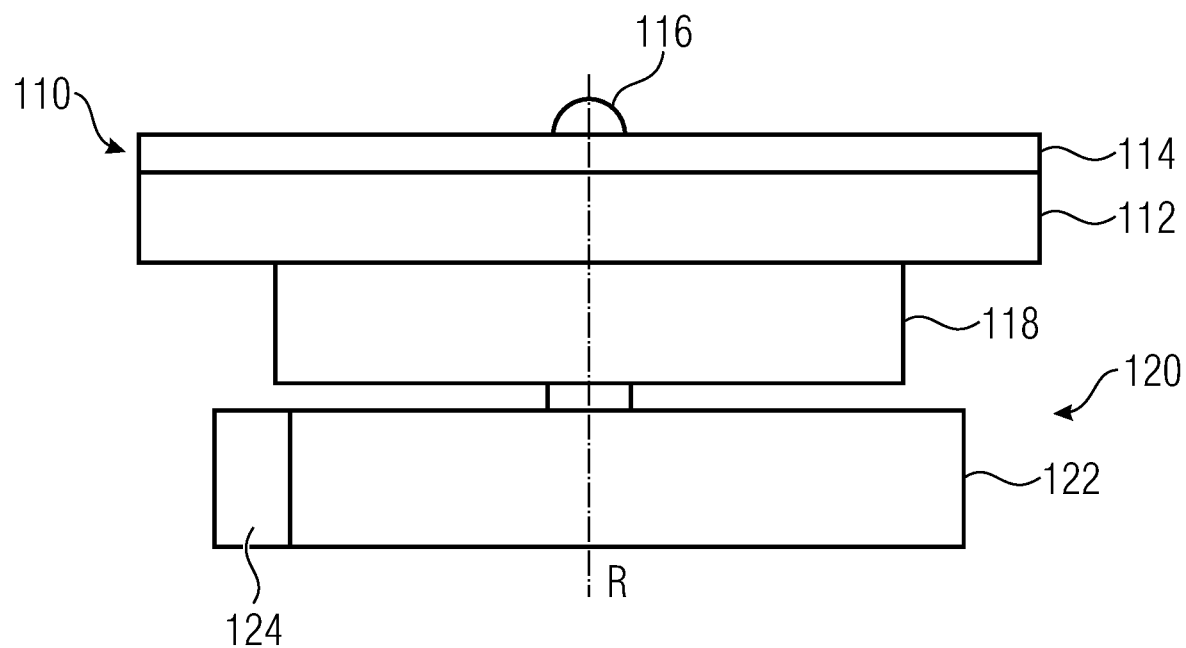
FIGS. 5A and 5B are schematic representations of devices for switching liquids utilizing fluidics modules as described herein.
Figure 5B:
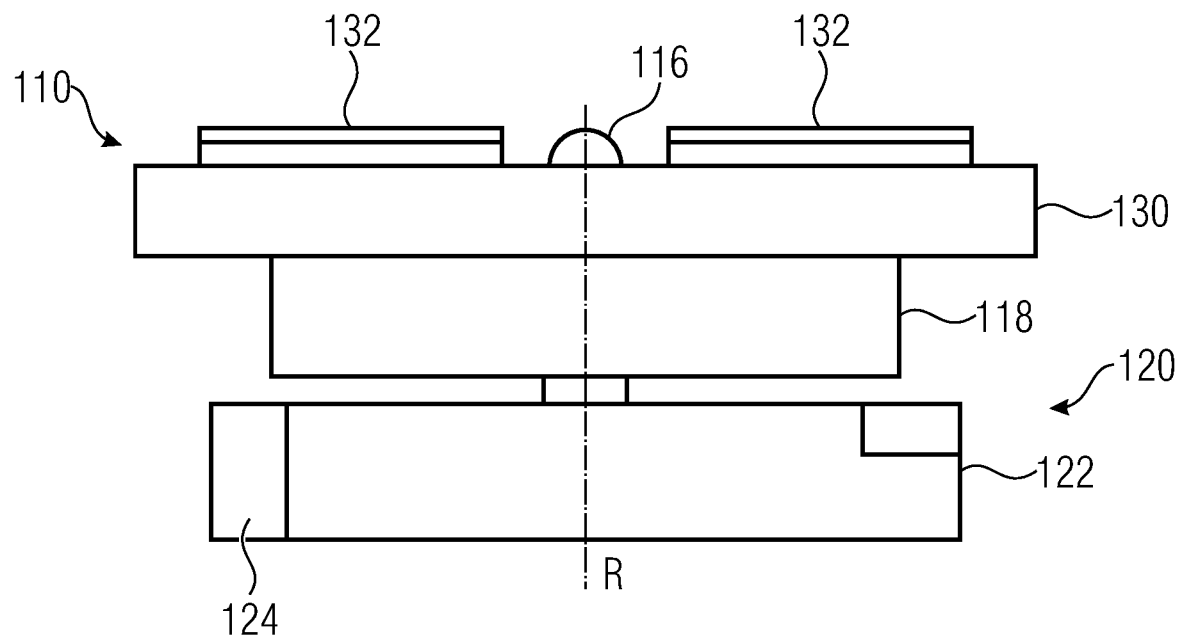

Referring to FIGS. 5A and 5B, examples of centrifugal microfluidic systems are described, utilizing or comprising a fluidics module as described herein. In other words, the fluidics module in the systems of FIGS. 5A and 5B may be any of the fluidics modules described herein.

FIG. 5A shows a device with a fluidics module 110 in the form of a rotating body having a substrate 112 and a cover 114. The substrate 112 and the cover 114 may be circular in plan view, with a central opening through which the rotating body 110 can be attached to a rotating part 118 of a drive device 120 via a conventional attachment device 116. The rotating part 118 is rotatably mounted on a stationary part 122 of the drive device 120. The drive device 120 may be, for example, a conventional centrifuge, which may have an adjustable rotational speed, or a CD or DVD drive. A control device 124 may be provided, which is configured to control the drive device 120 to impart rotation or rotations of different rotational frequencies to the rotating body 110. The control device 124 may, as will be apparent to those skilled in the art, be implemented by, for example, an appropriately programmed computing device or a user-specific integrated circuit. The control device 124 may further be configured to, in response to manual input from a user, control the drive device 120 to effect the rotations of the rotational body. In either case, the control device 124 may be configured to control the drive device 120 to impart the rotation to the rotational body to implement embodiments of the invention as described herein. The drive device 120 may be a conventional centrifuge having only one direction of rotation.

The rotating body 110 has the fluidics structures. The fluidics structures may be formed by cavities and channels in the cover 114, the substrate 112, or in the substrate 112 and the cover 114. In embodiments, for example, fluidics structures may be formed in the substrate 112, while fill openings and vent openings are formed in the cover 114. In embodiments, the structured substrate (including fill openings and vent openings) is arranged at the top and the cover is arranged at the bottom.

In an alternative embodiment shown in FIG. 5B, fluidics modules 132 are inserted into a rotor 130 and together with the rotor 130 form the rotating body 110. The fluidics modules 132 may each have a substrate and a cover, in which in turn corresponding fluidics structures may be formed. The rotating body 110 formed by the rotor 130 and the fluidics modules 132 in turn may be subjected to rotation by a drive device 120 controlled by the control device 124.

In FIGS. 5A and 5B, the center of rotation about which the fluidics module or the rotational body is rotatable is again referred to by R.

In embodiments of the invention, the fluidics module or rotating body comprising the fluidics structures may be formed from any suitable material, for example plastic such as PMMA (polymethyl methacrylate), PC (polycarbonate), PVC (polyvinyl chloride) or PDMS (polydimethylsiloxane), glass or the like. The rotating body 110 may be considered to be a centrifugal microfluidic platform. In embodiments, the fluidics module or rotating body may be formed from a thermoplastic, such as PP (polypropylene), PC, COP (cyclic olefin polymer), COC (cyclo olefin copolymer) or PS (polystyrene).

Examples of the present disclosure thus provide devices and methods for selectively switching liquids in centrifugal microfluidic cartridges. By means of the described structures in combination with the described methods, in the field of centrifugal microfluidics, several requirements for the unit operation of retaining and later selectively switching a liquid can be fulfilled simultaneously. It is possible to initiate the switching process using various changes in the process conditions (volume siphon, inertia). It is possible to generate a negative pressure with a waste liquid no longer required. It is also possible to generate the negative pressure using some of the process liquid no longer required. It is possible to make further adjustments to the fluidic structure in order to determine the process conditions for triggering a switching process over a wide range. The associated fluidic structures can be realized monolithically in a centrifugal microfluidic cartridge. The fluidic structures can also be implemented such that the functional principle is largely independent of the properties of the liquid and cartridge material. This includes, in particular, the contact angle between the liquid and the cartridge material as well as the viscosity and surface tension of the liquid.

Examples of the disclosure provide a rotating body having a structure including a first number of chambers as liquid reservoirs or reaction chambers, a second number of chambers, the first number of chambers being connected to the second number of chambers by a channel or another obstacle (e.g. filter membrane) with a high fluid resistance, the second number of chambers being connected to a fourth number of chambers such that, after the fluid from the second number of chambers enters the fourth number of chambers, under rotation, a negative pressure is created in the second number of chambers and there is a further connection from the second number of chambers to a third number of chambers, the third number of chambers being connected to the first number of chambers by a barrier, such as a siphon, wherein the negative pressure is transferred from the second number of chambers into the third number of chambers and thus the barrier is overcome due to this negative pressure, for example the siphon is filled with liquid, and subsequently the liquid is transferred from the first number of chambers directly into the third number of chambers.

In examples of such a structure, the connection from the second number of chambers to the fourth number of chambers is a siphon which is filled starting from a certain volume which has flowed into the second number of chambers, thereby initiating the generation of the negative pressure. In other examples of such a structure, the second number of chambers has a partition wall which is overflowed by the liquid flowing on the connection located behind the partition wall to the fourth number of chambers, due to the Euler force generated by the change in rotation, thereby generating the negative pressure in the second number of chambers. In examples of such a structure, the obstacle of high fluidic resistance between the first number of chambers and the second number of chambers is a filter membrane. In examples, the obstacle of high fluidic resistance between the first number of chambers and the second number of chambers is a channel of a diameter smaller than 100 μm.

Although features of the invention have each been described in terms of device features or method features, it is obvious to those skilled in the art that corresponding features may also be part of a method or device. Thus, the device may be configured to perform corresponding method steps, and the respective functionality of the device may represent corresponding method steps.

In the above detailed description, various features have been partly grouped together in examples to rationalize the disclosure. This type of disclosure is not to be interpreted as intending the claimed examples to have more features than are expressly stated in each claim. Rather, as the following claims reflect, subject-matter may lie in fewer than all the features of a single disclosed example. Consequently, the following claims are hereby incorporated into the detailed description, wherein each claim may stand as its own separate example. While each claim may stand as its own separate example, it should be noted that although dependent claims in the claims refer back to a specific combination with one or more other claims, other examples also include a combination of dependent claims with the subject-matter of any other dependent claim or a combination of any feature with other dependent or independent claims. Such combinations are included unless it is stated that a specific combination is not intended. Furthermore, a combination of features of a claim with any other independent claim is intended to be also encompassed, even if that claim is not directly dependent on the independent claim.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A method for handling liquid using a fluidics module comprising:
    first fluidics structures comprising a first fluid chamber,
    second fluidics structures comprising a second fluid chamber,
    a first fluidic connection comprising a fluidic resistance between the first fluid chamber and the second fluid chamber,
    third fluidics structures comprising a third fluid chamber,
    a second fluidic connection between the first fluid chamber and the third fluid chamber, the second fluidic connection comprising a barrier, the barrier comprising an inverted siphon, a capillary valve, a geometric valve or a fluid channel, the opening of which into the third fluid chamber is located radially further inwards than its opening into the first fluid chamber, wherein the flow resistance of the first fluidic connection is higher than the flow resistance of the second fluidic connection,
    a pressure compensation channel between the second fluid chamber and the third fluid chamber, and
    fourth fluidics structures comprising a fourth fluid chamber, which is connected to the second fluidics structures via a third fluidic connection,
    wherein a) the second fluidics structures comprise a partition wall between a first chamber portion of the second fluid chamber, into which the first fluidic connection opens, and a second chamber portion of the second fluid chamber, into which the third fluidic connection opens, which can be flown over by the liquid in the second fluid chamber due to an Euler force generated by a change in rotational speed of the fluidics module, or b) the third fluidic connection comprises an inverted siphon,
    the method comprising:
    rotating the fluidics module to generate a centrifugal force at which the fluidic resistance of the first fluidic connection is overcome, but not the barrier to transfer liquid centrifugally under rotation from the first fluid chamber through the fluidic resistance of the first fluidic connection into the second fluid chamber, while the barrier of the second fluidic connection initially prevents liquid from passing from the first fluid chamber into the third fluid chamber,
    wherein, when rotating, at least some of the liquid is transferred from the second fluid chamber via the third fluidic connection into the fourth fluid chamber under rotation by, if feature b) is fulfilled, an apex of the inverted siphon of the third fluidic connection to be wetted completely by the liquid transferred into the second fluid chamber, or, if feature a) is fulfilled, the rotational speed to be changed in order for the liquid transferred into the second fluid chamber to flow over the partition wall in order to generate a negative pressure in the second fluid chamber and the third fluid chamber, which is connected to the second fluid chamber via the pressure compensation channel, and
    wherein the barrier in the second fluidic connection is overcome by liquid from the first fluid chamber due to the generated negative pressure to transfer liquid from the first fluid chamber to the third fluid chamber via the second fluidic connection while the fluidic resistance of the first fluidic connection prevents liquid from passing by the liquid falling below a certain hydrostatic height in the first fluid chamber, and/or by reducing the rotational speed, since the fluidic resistance of the first fluidic connection and the barrier are implemented relative to each other in such a way that the negative pressure in the second fluid chamber and the third fluid chamber draws liquid into the third fluid chamber mainly through the second fluidic connection via the barrier and not into the second fluid chamber via the fluidic resistance.

2. The method according to claim 1, wherein the first fluidic connection comprises a fluid channel with a flow cross-section of less than 40.000 µm².

3. The method according to claim 1, wherein the first fluidic connection comprises a filter membrane and a fluid chamber separated from the first fluid chamber by the filter membrane.

4. The method according to claim 1, wherein a biomolecule- or cell-binding matrix is arranged in the first fluid chamber.

5. The method according to claim 1, wherein rotating the fluidics module comprises rotating at a first rotational speed to transfer the liquid from the first fluid chamber to the second fluid chamber, and rotating at a second rotational speed different from the first rotational speed to transfer the liquid from the first fluid chamber to the third fluid chamber due to the generated negative pressure.

6. The method according to claim 1, wherein the first fluidic connection comprises a filter membrane and a fluid chamber separated from the first fluid chamber by the filter membrane, wherein rotating is performed to transfer a permeate passing the filter membrane into the second fluid chamber, and to transfer a retentate retained by the membrane with the liquid due to the generated negative pressure from the first fluid chamber via the second fluidic connection into the third fluid chamber.

7. The method according to claim 1, comprising:
    introducing a sample liquid into the first fluid chamber comprising a biomolecule- or cell-binding matrix to bind biomolecules or cells to the matrix,
    performing rotating the fluidics module to transfer the sample liquid from the first fluid chamber to the second fluid chamber;
    introducing a washing solution into the first fluid chamber to remove impurities,
    performing rotating to transfer the washing solution from the first fluid chamber to the second fluid chamber,
    introducing an elution solution or lysis reagent into the first fluid chamber to elute the purified biomolecules or lyse cells and produce an eluate or lysate,
    performing rotating to transfer the washing solution and the sample solution at least partially from the second fluid chamber into the fourth fluid chamber to create the negative pressure and thereby transfer the eluate or lysate from the first fluid chamber to the third fluid chamber.

* * * * *